United States Patent
Mou et al.

(10) Patent No.: US 10,775,289 B2
(45) Date of Patent: Sep. 15, 2020

(54) GAS DETECTING DEVICE

(71) Applicant: Microjet Technology Co., Ltd., Hsinchu (TW)

(72) Inventors: Hao-Jan Mou, Hsinchu (TW); Hung-Chun Hu, Hsinchu (TW); Young-Chih Kuo, Hsinchu (TW); Jui-Yuan Chu, Hsinchu (TW); Chien-Chih Huang, Hsinchu (TW); Wen-Hsiung Liu, Hsinchu (TW); Yi-Cheng Huang, Hsinchu (TW); Wei-Chen Liao, Hsinchu (TW); Chi-Chiang Hsieh, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 0 days.

(21) Appl. No.: 16/223,896

(22) Filed: Dec. 18, 2018

(65) Prior Publication Data
US 2019/0234851 A1 Aug. 1, 2019

(30) Foreign Application Priority Data

Jan. 26, 2018 (TW) .............................. 107102942 A
Aug. 30, 2018 (TW) .............................. 107130414 A

(51) Int. Cl.
*G01N 15/06* (2006.01)
*G01N 15/02* (2006.01)
(Continued)

(52) U.S. Cl.
CPC ......... *G01N 15/0211* (2013.01); *G01N 15/06* (2013.01); *G01N 15/1459* (2013.01);
(Continued)

(58) Field of Classification Search
CPC .. G01N 21/47; G01N 21/59; G01N 2201/021; G01N 2201/0612;
(Continued)

(56) References Cited

U.S. PATENT DOCUMENTS 4,790,650 A * 12/1988 Keady .................. G01N 15/065
356/337
7,173,257 B1 * 2/2007 Warrick ............. G01N 15/0255
250/458.1
(Continued)

FOREIGN PATENT DOCUMENTS

CN 106233119 A 12/2016
JP 2002-122530 A 4/2002
(Continued)

OTHER PUBLICATIONS

Extended European Search Report, dated Jun. 26, 2019, for European Application No. 18213479.1.

*Primary Examiner* — Michael P Stafira
(74) *Attorney, Agent, or Firm* — Birch, Stewart, Kolasch & Birch, LLP

(57) ABSTRACT

A gas detecting device includes a casing, an optical mechanism, a gas transporting actuator, a laser module, a particle detector and an external sensing module. The casing includes a chamber, an inlet, an outlet and a communication channel. The optical mechanism is disposed in the chamber. The optical mechanism includes an airflow channel and a light-beam channel. The airflow channel is in fluid communication with the at least one inlet and the outlet. The light-beam channel is in communication with the airflow channel. The gas transporting actuator is disposed on the optical mechanism. The laser module is disposed in the optical mechanism for emitting a light beam to the airflow channel. The particle detector detects sizes and a concen- (Continued)

tration of the suspended particles in the air. The external sensing module is installed in the communication channel to measure the air.

20 Claims, 14 Drawing Sheets

(51) Int. Cl.
  *G01N 15/14* (2006.01)
  *G01N 33/00* (2006.01)
  G01N 15/00 (2006.01)
(52) U.S. Cl.
  CPC ..... *G01N 33/0031* (2013.01); *G01N 15/1436* (2013.01); *G01N 33/0029* (2013.01); *G01N 33/0036* (2013.01); *G01N 2015/0046* (2013.01); *G01N 2015/0693* (2013.01); *G01N 2015/1486* (2013.01); *G01N 2015/1493* (2013.01)
(58) Field of Classification Search
  CPC ............. G01N 2201/062; G01N 15/06; G01N 2015/0046; G01N 2015/0693; G01N 2001/2223; G01N 15/1459; G01N 15/0205; G01N 15/0211; G01N 1/2273; G01N 15/0656; G01N 1/2205; G01N 2015/1486; G01N 15/065; G01N 2015/0038; G01N 21/53; G01N 15/0227; G01N 15/0266; G01N 15/1404; G01N 2015/0053; G01N 2015/0065; G01N 33/0031; G01N 15/0606; G01N 15/14; G01N 15/1434; G01N 15/1436; G01N 15/1484; G01N 1/10; G01N 1/14; G01N 1/22; G01N 1/34; G01N 1/38; G01N 1/4077; G01N 1/44; G01N 2001/4088; G01N 2015/149; G01N 2015/1493; G01N 2035/00455; G01N 21/3577; G01N 21/85; G01N 33/0009; G01N 33/0014; G01N 33/0022; G01N 33/0036; G01N 33/0073; G01N 33/6893; G01N 15/02; G01N 15/0255; G01N 15/0612; G01N 15/0618; G01N 15/0826; G01N 15/088; G01N 15/10; G01N 15/1056; G01N 15/1425; G01N 15/1468; G01N 15/147; G01N 17/002; G01N 1/2208; G01N 1/2211; G01N 1/2214; G01N 1/2226; G01N 1/28; G01N 2001/2241; G01N 2001/2255; G01N 2001/2261; G01N 2001/2264; G01N 2001/2282; G01N 2001/2893; G01N 2001/385; G01N 2015/0019; G01N 2015/003; G01N 2015/008; G01N 2015/0294; G01N 2015/0687; G01N 2015/084; G01N 2015/0846; G01N 2015/1006; G01N 2015/1075; G01N 2015/1081; G01N 2015/142; G01N 2015/1454; G01N 2015/1481; G01N 2015/1497; G01N 2021/151; G01N 2021/1734; G01N 2021/1761; G01N 2021/3595; G01N 2021/4711; G01N 2021/8578; G01N 21/05; G01N 21/17; G01N 21/278; G01N 21/4738; G01N 21/4785; G01N 21/532; G01N 2201/06113; G01N 2201/12; G01N 2333/775; G01N 33/0029; G01N 33/0032; G01N 33/0037; G01N 33/004; G01N 33/0047; G01N 33/0065; G01N 33/0075; G01N 33/18; G01N 33/2835; G01N 33/2841; G01N 33/2847; G01N 33/2858; G01N 33/48; G01N 33/487; G01N 33/5091; G01N 33/54306; G01N 33/54366; G01N 33/56983; G01N 33/574; G01N 33/92; G02B 6/0001
  See application file for complete search history.

(56) References Cited

U.S. PATENT DOCUMENTS

| 2013/0276517 | A1* | 10/2013 | Takano ................... G01M 3/18 73/40.5 R |
|---|---|---|---|
| 2015/0041681 | A1 | 2/2015 | Fujita et al. |
| 2016/0153884 | A1* | 6/2016 | Han ...................... G01N 1/2205 |
| 2017/0023457 | A1* | 1/2017 | Hart ........................ G01N 15/06 |
| 2017/0328825 | A1* | 11/2017 | Godoy ............... G01N 15/0211 |

FOREIGN PATENT DOCUMENTS

| TW | M525446 U | 7/2016 |
|---|---|---|
| TW | M554535 U | 1/2018 |
| WO | WO 2010/140001 A1 | 12/2010 |

* cited by examiner

GAS DETECTING DEVICE

FIELD OF THE INVENTION

The present disclosure relates to a gas detecting device, and more particularly to a gas detecting device having a gas transporting actuator for gas transportation.

BACKGROUND OF THE INVENTION

Recently, the air pollution problems are becoming increasingly serious in our country and its neighboring regions. In particular, the concentration of fine suspended particles (e.g., Particulate Matter 2.5, PM2.5 and Particulate Matter 10, PM10) is often too high. Hence, the monitoring of the concentration of suspended particles in the air is getting attention. However, since the air flows with the change of the wind direction and the air volume and the current air quality monitoring stations for detecting suspended particles are mostly fixed points, it is impossible to confirm the concentration of suspended particles in the current surroundings. Hence, a miniature portable gas detecting device is needed. It allows users to detect the concentration of suspended particles around the surrounding anytime and anywhere.

Moreover, the current gas detecting device is often only capable of detecting a single gas. In addition to the suspended particles, there are many gases harmful to the human body in daily life. If the harmful gases cannot be detected immediately, the health of the human body is adversely affected.

Moreover, the user's demands for detecting different gases may be varied according to different places (e.g., factories, offices or homes). For example, the gas sensors for detecting the volatile gases or the toxic gases (e.g., the gases that cause the inhalation injuries) are suitably used in factories. The carbon monoxide sensors, the carbon dioxide sensors, the temperature sensors or the humidity sensors are suitably used in homes or offices. Since the commercially available gas detecting device is an integral gas detecting device, some drawbacks occur. For example, the type of the gas to be detected has been determined before the gas detecting device leaves the factory. The type of the gas to be detected cannot be changed by the user according to the user's requirement. Consequently, the gas detecting device detects the gas out of the user's requirement or fails to detect the gas according to the user's requirement. In other words, the conventional gas detecting device is not user-friendly. Moreover, it is difficult for the user to select the suitable gas detecting device. For solving the above drawbacks, it is important to provide a gas detecting device for detecting the gas according to the user's requirement.

SUMMARY OF THE INVENTION

An object of the present disclosure provides a gas detecting device. The gas detecting device is capable of detecting a concentration of the suspended particles and other gas concentration in the air so as to provide a user with air information timely and accurately. The sensor for detecting the gas is an external sensor. The sensor may be selected and replaced easily by the user according to the practical requirement, so that the gas detecting device is user-friendly.

In accordance with an aspect of the present disclosure, a gas detecting device is provided. The gas detecting device includes a casing, an optical mechanism, a gas transporting actuator, a laser module, a particle detector and at least one external sensing module. The casing includes a chamber, at least one inlet, an outlet and at least one communication channel. The chamber is in fluid communication with the inlet, the outlet and the communication channel. The optical mechanism is disposed in the chamber and has an airflow channel and a light-beam channel. The airflow channel is in fluid communication with the inlet and the outlet. The light-beam channel is in communication with the airflow channel. The gas transporting actuator is disposed on the optical mechanism. When the gas transporting actuator is actuated, an ambient air is introduced through the inlet into the chamber and transferred through the communication channel to the airflow channel. The laser module is disposed in the optical mechanism for emitting a light beam through the light-beam channel to the airflow channel. The particle detector is disposed in the airflow channel and located at a first end of the airflow channel away from the gas transporting actuator. The particle detector detects a plurality of light spots caused by the suspended particles in the air after the light beam from the laser module is projected on the air within the airflow channel and accordingly calculates sizes and a concentration of the suspended particles in the air. The at least one external sensing module is detachably installed in the communication channel and includes a sensor for measuring the air within the communication channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
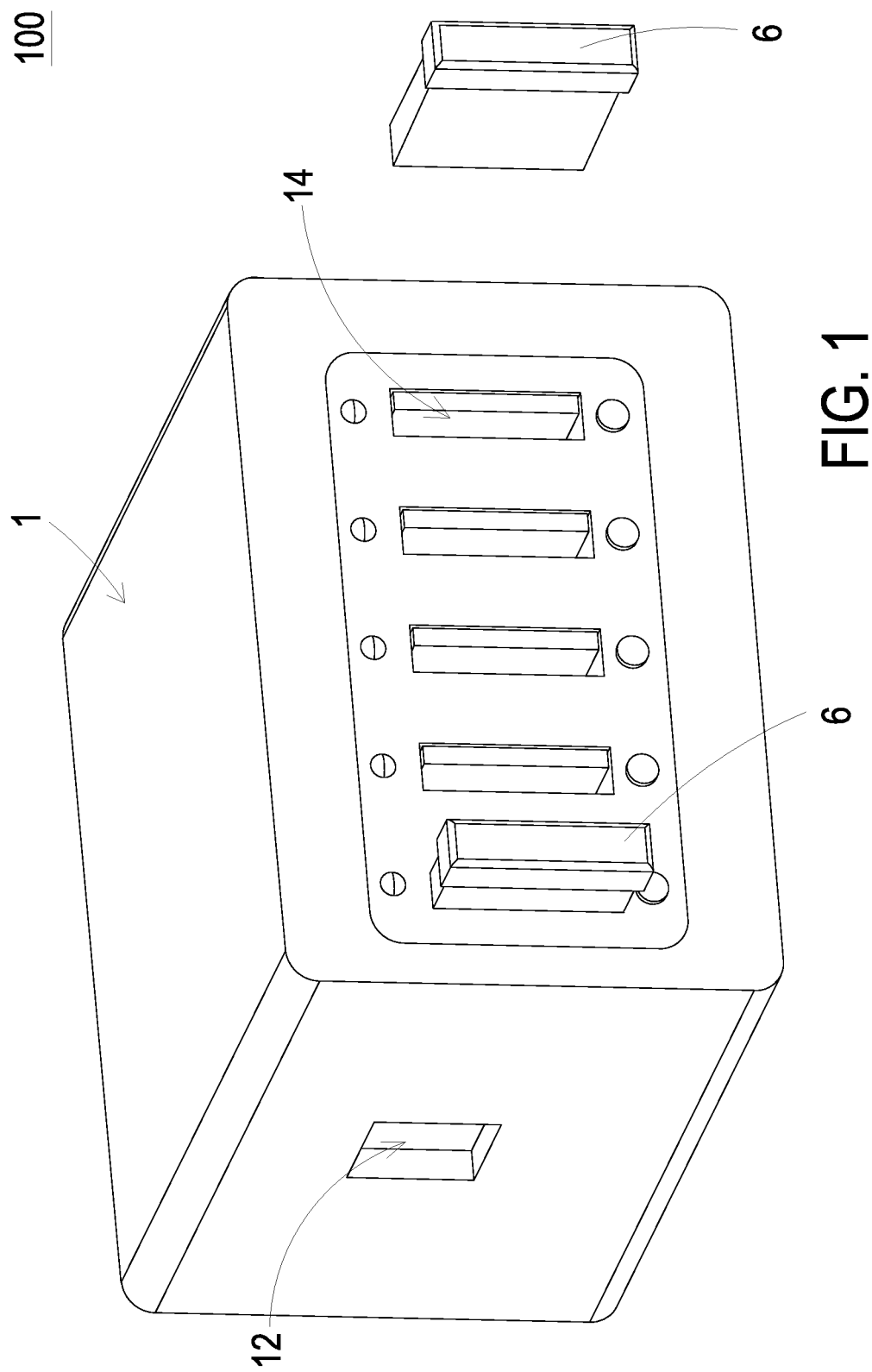
FIG. 1 is a schematic perspective view illustrating a gas detecting device according to a first embodiment of the present disclosure.
Figure 2:
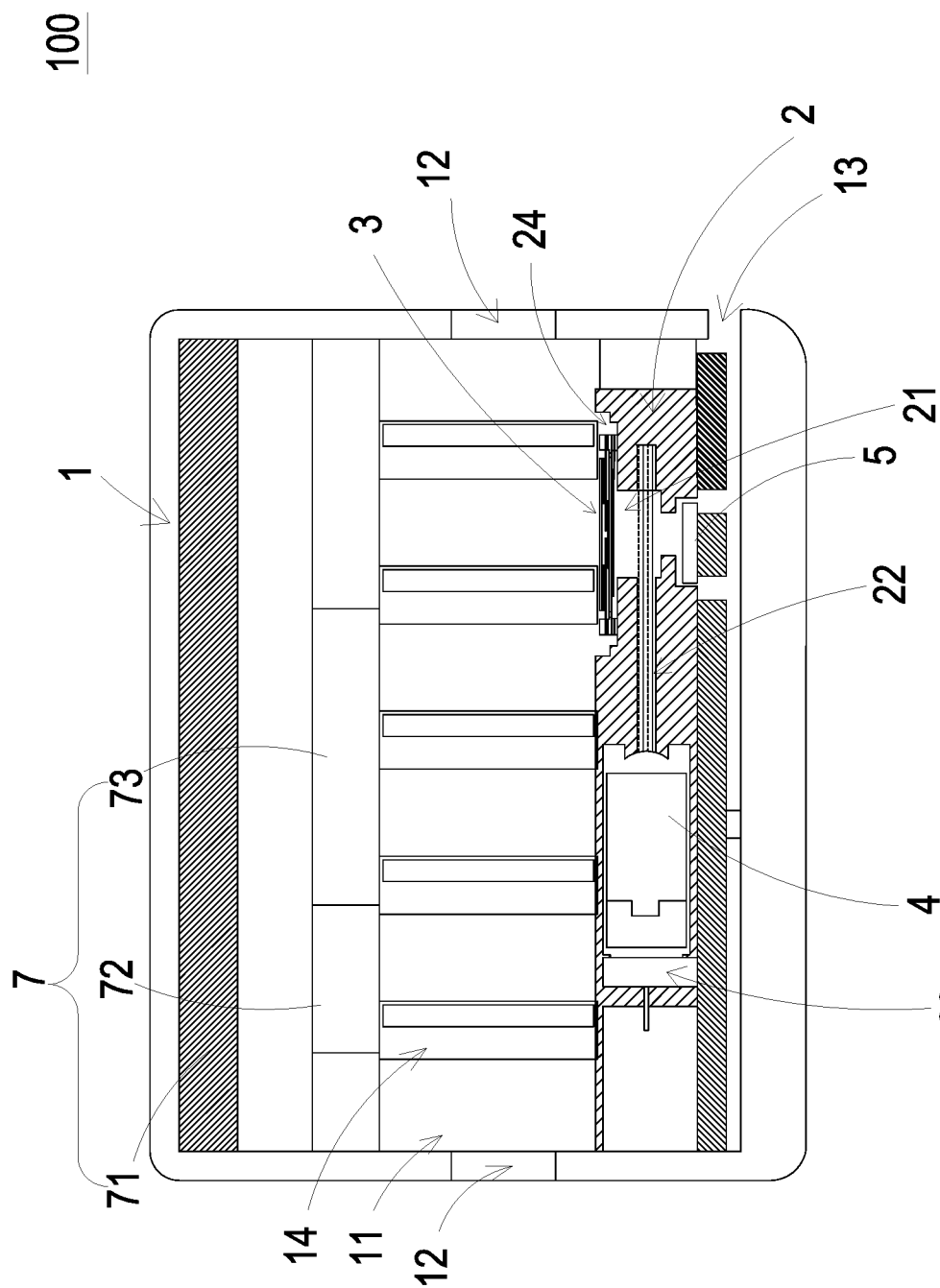
FIG. 2 is a schematic cross-sectional view illustrating a portion of the gas detecting device according to the first embodiment of the present disclosure.

Please refer to FIGS. 1 and 2. The present discourse provides a gas detecting device 100 including at least one casing 1, at least one optical mechanism 2, at least one gas transporting actuator 3, at least one laser module 4, at least one particle detector 5 and at least one external sensing module 6. The casing 1 includes at least one chamber 11, at least one inlet 12, at least one outlet 13 and at least one communication channel 14. The optical mechanism 2 includes at least one airflow channel 21 and at least one light-beam channel 22. The number of the casing 1, the chamber 11, the outlet 13, the optical mechanism 2, the airflow channel 21, the light-beam channel 22 and the gas transporting actuator 3 is exemplified by one for each in the following embodiments but not limited thereto. It is noted that each of the casing 1, the chamber 11, the outlet 13, the optical mechanism 2, the airflow channel 21, the light-beam channel 22 and the gas transporting actuator 3 can also be provided in plural numbers.

The present disclosure provides a gas detecting device 100. Please refer to FIGS. 1 and 2. In this embodiment, the gas detecting device 100 includes a casing 1, an optical mechanism 2, a gas transporting actuator 3, a laser module 4, a particle detector 5 and at least one external sensing module 6. The casing 1 includes a chamber 11, at least one inlet 12, an outlet 13 and at least one communication channel 14. The chamber 11 is in fluid communication with the at least one inlet 12, the outlet 13 and the at least one communication channel 14. The optical mechanism 2 is disposed in the chamber 11 of the casing 1 and has an airflow channel 21 and a light-beam channel 22. The airflow channel 21 is in fluid communication with the at least one inlet 12 and the outlet 13. The light-beam channel 22 is in communication with the airflow channel 21. The gas transporting actuator 3 is disposed on the optical mechanism 2. When the gas transporting actuator 3 is actuated to change the pressure in the interior of the chamber 11, the ambient air is introduced through the at least one inlet 12 into the chamber 11. Then, the air is transferred through the at least one communication channel 14 to the airflow channel 21. Afterwards, the air is discharged from the casing 1 through the outlet 13. The laser module 4 is disposed in the optical mechanism 2 for emitting a light beam. The light beam is transmitted through the light-beam channel 22 to the airflow channel 21. The particle detector 5 is disposed in the airflow channel 21 and located at a first end of the airflow channel 21 away from the gas transporting actuator 3. When the light beam from the laser module 4 is projected on the air within the airflow channel 21, the suspended particles in the air would generate a plurality of light spots. The particle detector 5 detects the plurality of light spots to calculate and obtain sizes and a concentration of the suspended particles in the air. The at least one external sensing module 6 is detachably installed in the at least one communication channel 14. The external sensing module 6 and the communication channel 14 are correspondingly assembled with each other. In this embodiment, the gas detecting device 100 includes five communication channels 14 and five external sensing modules 6. It is noted that the numbers of the at least one communication channel 14 and the at least one external sensing module 6 are not restricted. The external sensing module 6 includes a sensor (not shown). The sensor can be at least one selected from the group consisting of an oxygen sensor, a carbon monoxide sensor, a carbon dioxide sensor and combinations thereof. Alternatively, the sensor can be a volatile organic compound sensor. Alternatively, the sensor can be at least one selected from the group consisting of a bacterial sensor, a virus sensor, a microorganism sensor and combinations thereof. Alternatively, the sensor can be at least one selected from the group consisting of a temperature sensor, a humidity sensor and combinations thereof.

Please refer to FIG. 2. The optical mechanism 2 further includes a light-source receiving slot 23 and an accommodation slot 24. The laser module 4 is accommodated within the light-source receiving slot 23. The light-source receiving slot 23 is in communication with the light-beam channel 22. The accommodation slot 24 is located at a second end of the airflow channel 21 away from the particle detector 5, and the gas transporting actuator 3 is accommodated within the accommodation slot 24. When the gas transporting actuator 3 is actuated, the ambient air around the casing 1 is introduced through the inlet 12 into the chamber 11. Then, the air is transferred from the chamber 11 to the airflow channel 21 by the gas transporting actuator 3. Meanwhile, the light beam from the laser module 4 is transmitted through the light-beam channel 22 to the airflow channel 21 and projected on the air within the airflow channel 21, and the suspended particles in the air are irradiated by the light beam to generate scattering phenomenon. The particle detector 5 detects the light spots, which are generated as the suspended particles in the air are irradiated by light beam, to calculate and obtain the sizes and the concentration of the suspended particles in the air. The suspended particles may be PM2.5 suspended particles or PM10 suspended particles. In addition, the external sensing module 6 is detachably installed in the communication channel 14, which is in fluid communication with the chamber 11. The sensor of the external sensing module 6 senses the content of a specified gas in the air flowing into the communication channel 14, the content of other contaminate (e.g., the bacterial content, the virus content or the microorganism content) or the environment condition (e.g., temperature or humidity).

Figure 3A:
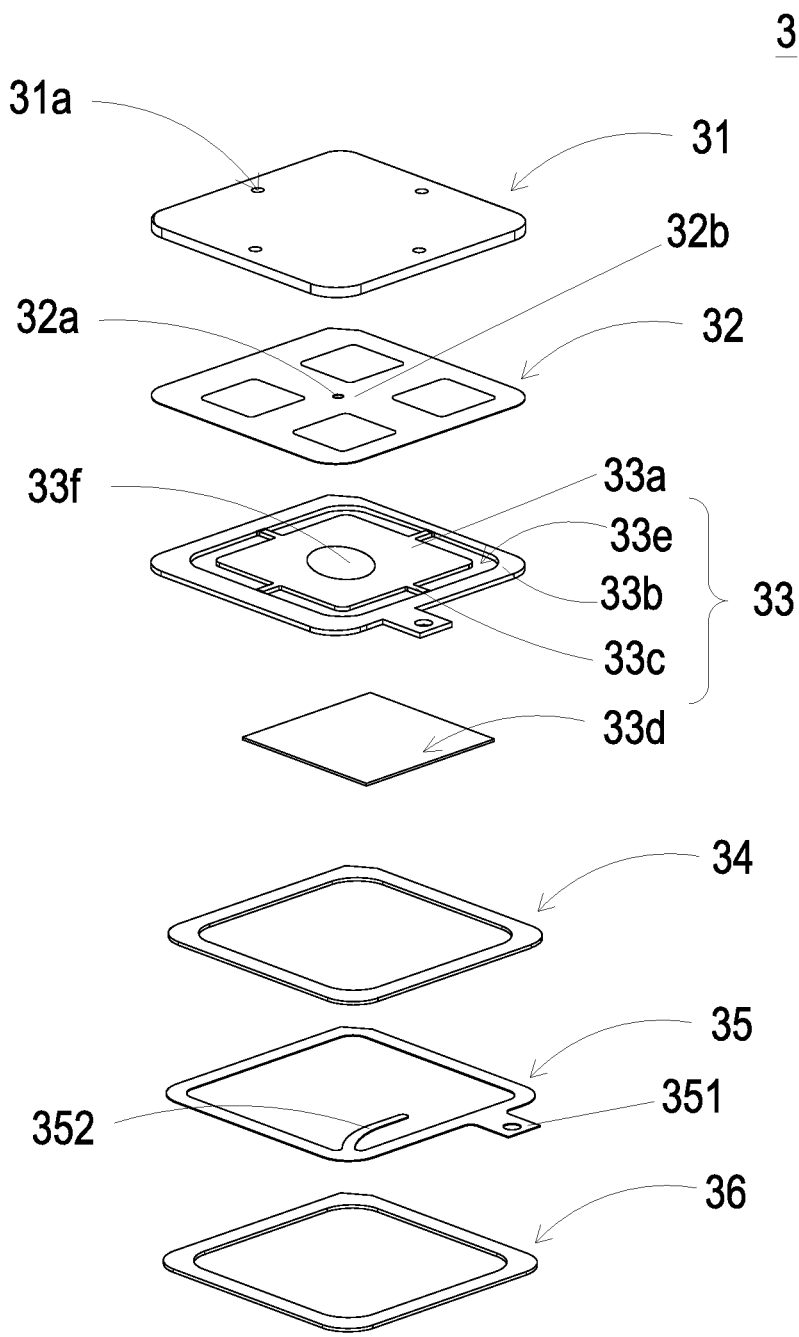
FIG. 3A is a schematic exploded view illustrating a gas transporting actuator of the gas detecting device according to the first embodiment and taken along the front side.
Figure 3B:
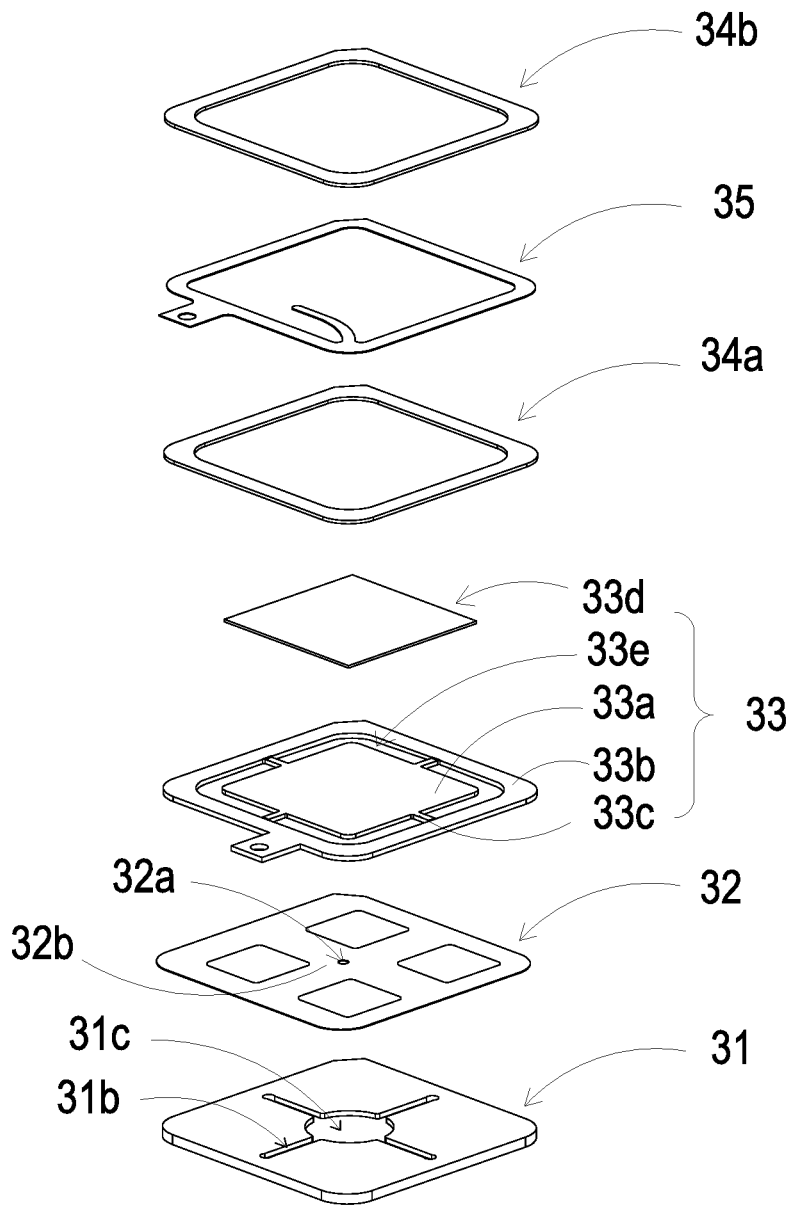
FIG. 3B is a schematic exploded view illustrating the gas transporting actuator of FIG. 3A and taken along the rear side.
Figure 4A:
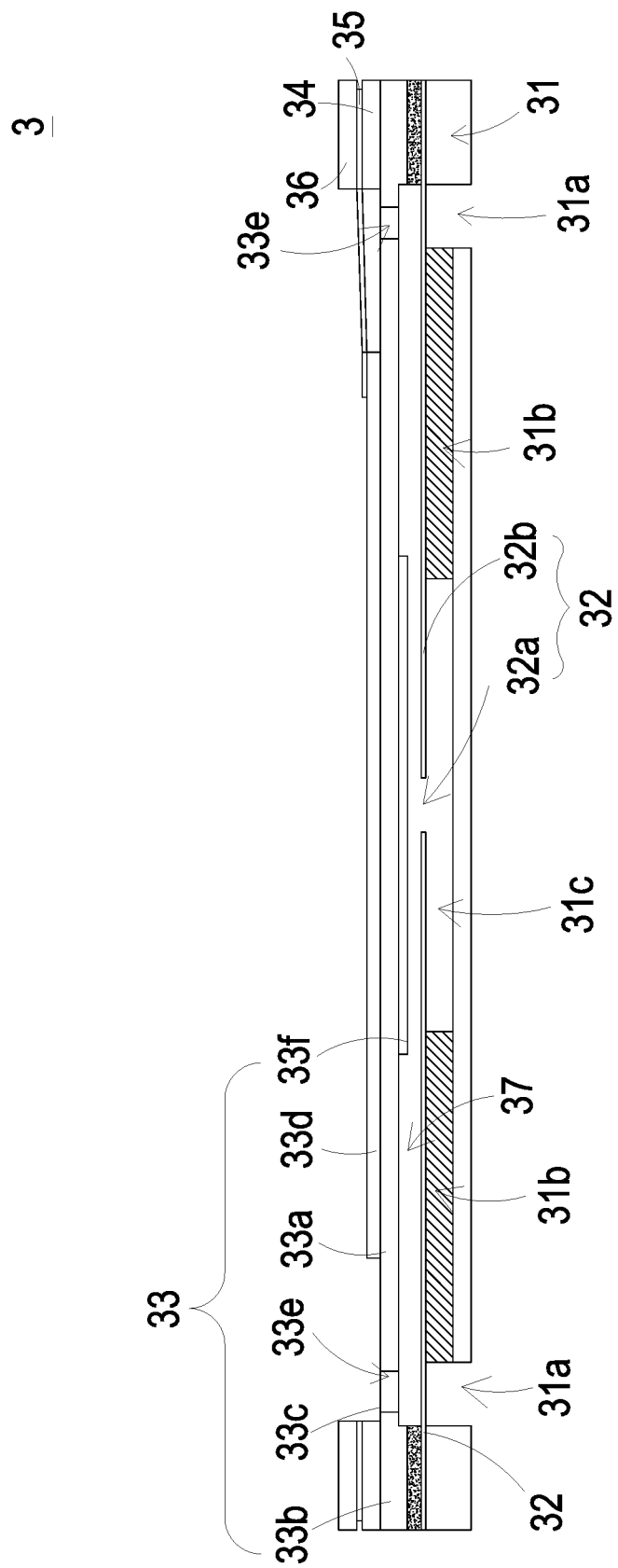
FIG. 4A is a schematic cross-sectional view illustrating the gas transporting actuator of the gas detecting device according to the first embodiment of the present disclosure.

Please refer to FIGS. 3A, 3B and 4A. In this embodiment, the gas transporting actuator 3 is a piezoelectric pump including a gas inlet plate 31, a resonance plate 32, a piezoelectric actuator 33, a first insulation plate 34, a conducting plate 35 and a second insulation plate 36. The gas inlet plate 31, the resonance plate 32, the piezoelectric actuator 33, the first insulation plate 34, the conducting plate 35 and the second insulation plate 36 are stacked on each other sequentially.

In this embodiment, the gas inlet plate 31 has at least one inlet aperture 31$a$, at least one convergence channel 31$b$ and a convergence chamber 31$c$. The at least one convergence channel 31$b$ is in communication with and corresponding in position to the at least one inlet aperture 31$a$. The inlet aperture 31$a$ allows the air to flow in, and the convergence channel 31$b$ guides the air from the inlet aperture 31$a$ toward the convergence chamber 31$c$. The resonance plate 32 has a central aperture 32$a$ and a movable part 32$b$. The central aperture 32$a$ is corresponding in position to the convergence chamber 31$c$ of the gas inlet plate 31. The movable part 32$b$ surrounds the central aperture 32$a$. A chamber space 37 is formed between the resonance plate 32 and the piezoelectric actuator 33. When the piezoelectric actuator 33 is actuated, the air is introduced through the at least one inlet aperture 31a of the gas inlet plate 31 into the at least one convergence channel 31b, and then the air is guided through the convergence channel 31b to the convergence chamber 31c. Then, the air is transferred through the central aperture 32a of the resonance plate 32. The movable part 32b of the resonance plate 32 is in resonance with the piezoelectric actuator 33 so as to transport the air.

Please refer to FIGS. 3A, 3B and 4A again. The piezoelectric actuator 33 includes a suspension plate 33a, an outer frame 33b, at least one bracket 33c and a piezoelectric element 33d. In this embodiment, the suspension plate 33a is a square suspension plate and is permitted to undergo bending vibration, but not limited thereto. The suspension plate 33a has a bulge 33E In this embodiment, in comparison with the circular suspension plate, the structure of the square suspension plate 33a is obviously more power-saving. Generally, the consumed power of the capacitive load at the resonance frequency is positively related to the resonance frequency. Since the resonance frequency of the square suspension plate 33a is lower than that of the circular suspension plate, the consumed power of the square suspension plate 33a is lower. However, in other embodiment, the profile of the suspension plate 33a may be varied according to the practical requirements. The outer frame 33b is arranged around the suspension plate 33a. The at least one bracket 33c is connected between the suspension plate 33a and the outer frame 33b for providing a supporting force to elastically support the suspension plate 33a. In an embodiment, a length of a side of the piezoelectric element 33d is smaller than or equal to a length of a side of the suspension plate 33a. The piezoelectric element 33d is attached on one surface of the suspension plate 33a. When a voltage is applied to the piezoelectric element 33d, the piezoelectric element 33d drives the suspension plate 33a to bend and vibrate. Moreover, at least one vacant space 33e is formed among the suspension plate 33a, the outer frame 33b and the at least one bracket 33c for allowing the air to pass therethrough. The bulge 33f is formed on the other surface of the suspension plate 33a. In this embodiment, the suspension plate 33a and the bulge 33f are integrally formed in one piece by an etching process, but not limited thereto.

Please refer to FIG. 4A. In this embodiment, there is a gap formed between the resonance plate 32 and the outer frame 33b of the piezoelectric actuator 33 so as to define the chamber space 37. The gap may be filled with a filler (e.g., a conductive adhesive) so that a depth from the resonance plate 32 to the suspension plate 33a can be maintained and the gas can be transferred rapidly. Moreover, the gap ensures the proper distance between the suspension plate 33a and the resonance plate 232, so that the contact interference is reduced and the generated noise is largely reduced. In some other embodiments, the height of the outer frame 33b of the piezoelectric actuator 33 is increased, so that the thickness of the conductive adhesive filled into the gap between the resonance plate 32 and the outer frame 33b of the piezoelectric actuator 33 can be reduced. Since the thickness of the conductive adhesive would be adversely affected by the laminating temperature or the cooling temperature during the process of assembling the overall gas transporting actuator 3, the reduction of the thickness of the conductive adhesive reduces such negative impact to maintain the proper distance between the suspension plate 33a and the resonance plate 32, and therefore the size of the chamber space 37 of the assembled gas transporting actuator 3 is not adversely affected by thermal expansion or contraction of the conductive adhesive. In other embodiment, the suspension plate 33a is formed by a stamping process. One surface of the bulge 33f of the suspension plate 33a away from the piezoelectric element 33d and one surface of the outer frame 33b away from the piezoelectric element 33d are not coplanar. That is, the surface of the bulge 33f away from the piezoelectric element 33d is at a level lower than the surface of the outer frame 33b away from the piezoelectric element 33d. After a filler (e.g., a conductive adhesive) is coated on the surface of the outer frame 33b away from the piezoelectric element 33d, the piezoelectric actuator 33 is attached on the resonance plate 32 by a hot laminating process. Consequently, the piezoelectric actuator 33 and the resonance plate 32 are assembled and combined together. Since the suspension plate 33a of the piezoelectric actuator 33 is formed by the stamping process, the structure of the chamber space 37 is improved. The chamber space 37 is formed by properly adjusting the stamping distance of the suspension plate 33a of the piezoelectric actuator 33, so that the method of designing and adjusting the chamber space 37 is effectively simplified. That is, the fabricating process is simplified and time-saving. In this embodiment, the first insulation plate 34, the conducting plate 35 and the second insulation plate 36 are frame-type thin plates, but not limited thereto.

Please refer to FIGS. 3A, 3B and 4A again. Each of the gas inlet plate 31, the resonance plate 32, the piezoelectric actuator 33, the first insulation plate 34, the conducting plate 35 and the second insulation plate 36 is produced by a surface micromachining technology of a microelectromechanical process, so that the volume of the gas transporting actuator 3 is effectively reduced to form a MEMS-type gas transporting actuator 3.

Figure 4B:
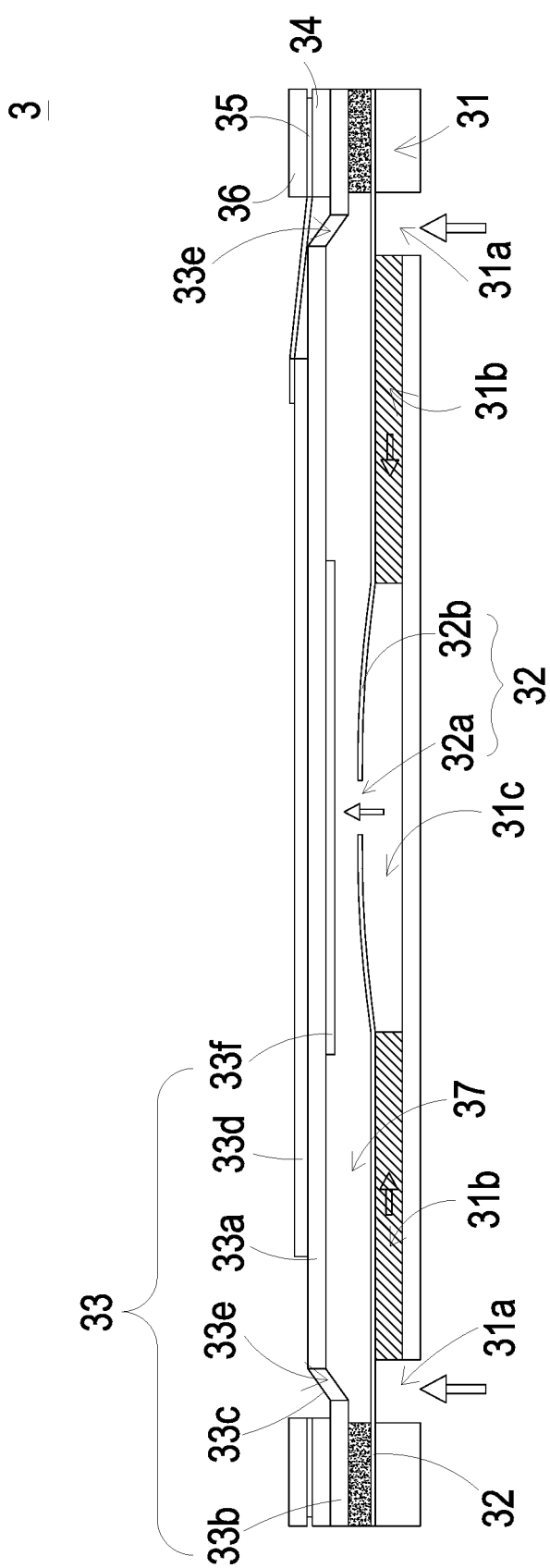
FIGS. 4B, 4C and 4D schematically illustrate the actions of the gas transporting actuator as shown in FIG. 4A.

Please refer to FIG. 4B. During the actions of the piezoelectric actuator 33, a voltage is applied to the piezoelectric element 33d of the piezoelectric actuator 33 so that the piezoelectric element 33d deforms to drive the suspension plate 33a to move in the direction away from the gas inlet plate 31. Meanwhile, the volume of the chamber space 37 is expanded, and a negative pressure is formed in the chamber space 37, so that the air in the convergence chamber 31c is inhaled into the chamber space 37. At the same time, the resonance plate 32 is in resonance with the piezoelectric actuator 33 and moved in the direction away from the gas inlet plate 31 synchronously, so that the volume of the convergence chamber 31c is expanded. Since the air in the convergence chamber 31c is transported to the chamber space 37, a negative pressure is also formed in the convergence chamber 31c. Consequently, the air is inhaled through the inlet 31a and the convergence channel 31b to the convergence chamber 31c.

Figure 4C:
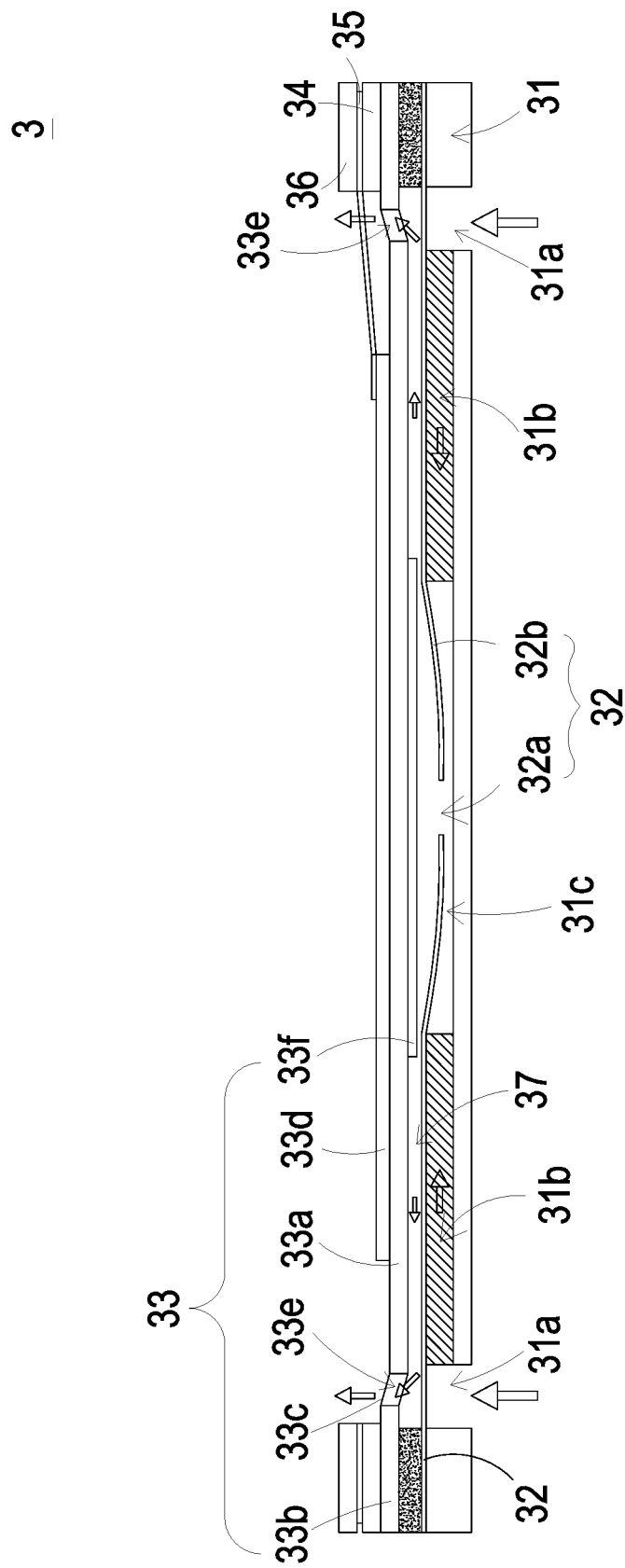

Then, as shown in FIG. 4C, the piezoelectric element 33d drives the suspension plate 33a to move in the direction toward the gas inlet plate 31, so that the volume of the chamber space 37 is shrunken. Meanwhile, the resonance plate 32 is in resonance with the suspension plate 33a and is actuated to move in the direction toward the gas inlet plate 31. The air in the chamber space 37 is pushed to flow through the vacant space 33e synchronously, so that the efficacy of transporting the air is achieved.

Figure 4D:
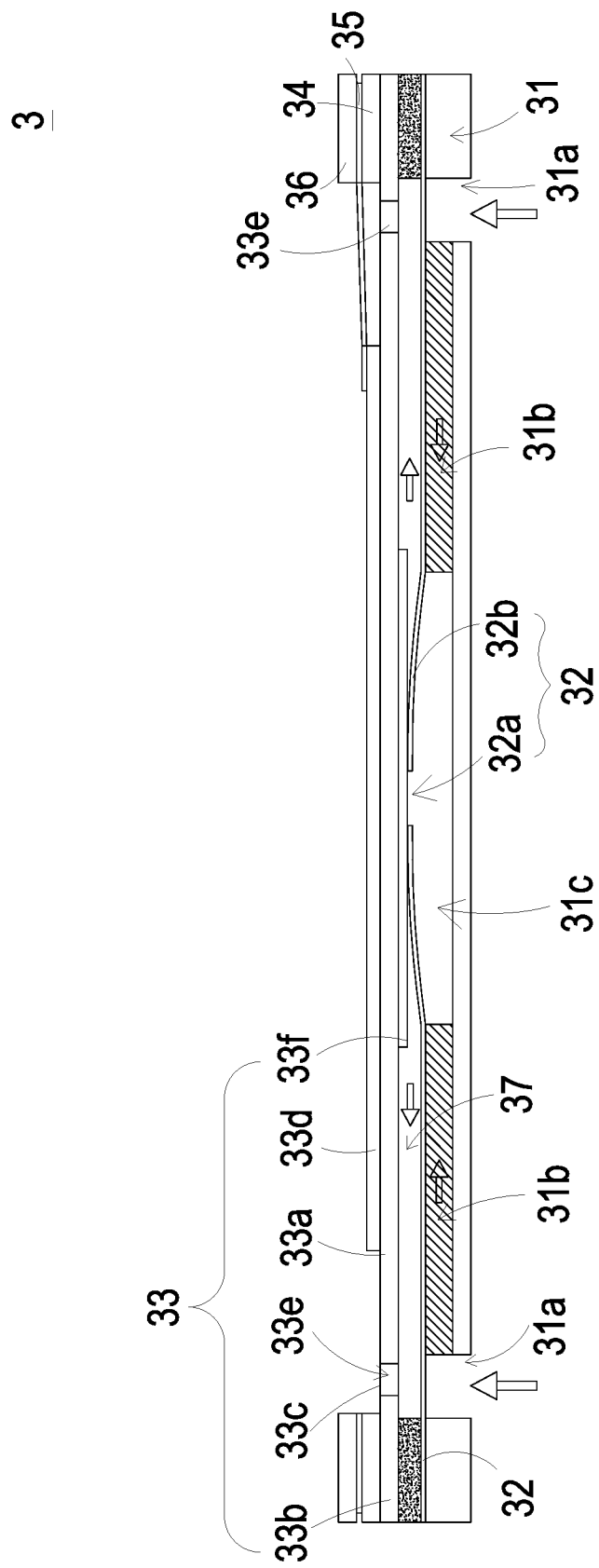

Finally, as shown in FIG. 4D, the suspension plate 33a is returned to its original position, where the piezoelectric element 33d fails to drive the suspension plate 33a, and the suspension plate 33a drives the resonance plate 32 to move in the direction away from the gas inlet plate 31. Meanwhile, the resonance plate 32 compresses the air in the chamber space 37 to transport the air to the vacant space 33e, and the volume of the convergence chamber 31c is expanded, so that the air can flow through the inlet aperture 31a and the convergence channel 31b and collected to the convergence chamber 31c continuously. The actions of the gas transporting actuator 3 as shown in FIGS. 4B, 4C and 4D are repeatedly done. Consequently, the gas transporting actuator 3 can transport the air at high speed continuously, so that the function of transporting and discharging the air by the gas transporting actuator 3 is achieved.

Please refer to FIGS. 3A, 3B and 4A again. The first insulation plate 34, the conducting plate 35 and the second insulation plate 36 are supported and stacked on the piezoelectric actuator 33 sequentially. The conducting plate 35 includes a conducting pin 351 protruded from an outer edge of the conducting plate 35 and an electrode 352 being a curve-shaped and protruded from an inner edge of the conducting plate 35. The electrode 352 is electrically connected to the piezoelectric element 33d of the piezoelectric actuator 33. The conducting pin 351 of the conducting plate 35 is electrically connected to an external circuit (not shown) to receive electricity from the external circuit to enable the piezoelectric element 33d of the piezoelectric actuator 33. In addition, the first insulation plate 34 and the second insulation plate 36 can prevent from the short-circuited problem.

In case that the suspended particles are deposited on the exterior surface of the particle detector 5, the detecting result of the particle detector 5 is not accurate enough. For addressing this problem, a cleaning process is required during the detecting process of the gas detecting device 100 or at any preset time spot. While the cleaning process is performed, the gas transporting actuator 3 is actuated to inhale the ambient gas into the inlet 12 and eject the air to the airflow channel 21 at a high speed. Thereby, the suspended particles on the exterior surface of the particle detector 5 are blown away so that the detecting accuracy of the particle detector 5 is enhanced. The timing of performing the cleaning process may be manually set by the user or automatically set by software according to the real-time monitored value. For example, the cleaning process is performed before the detecting task. Alternatively, the cleaning process is periodically performed at a plurality of time spots (e.g., 3 minutes) within a specified time interval.

Figure 5:
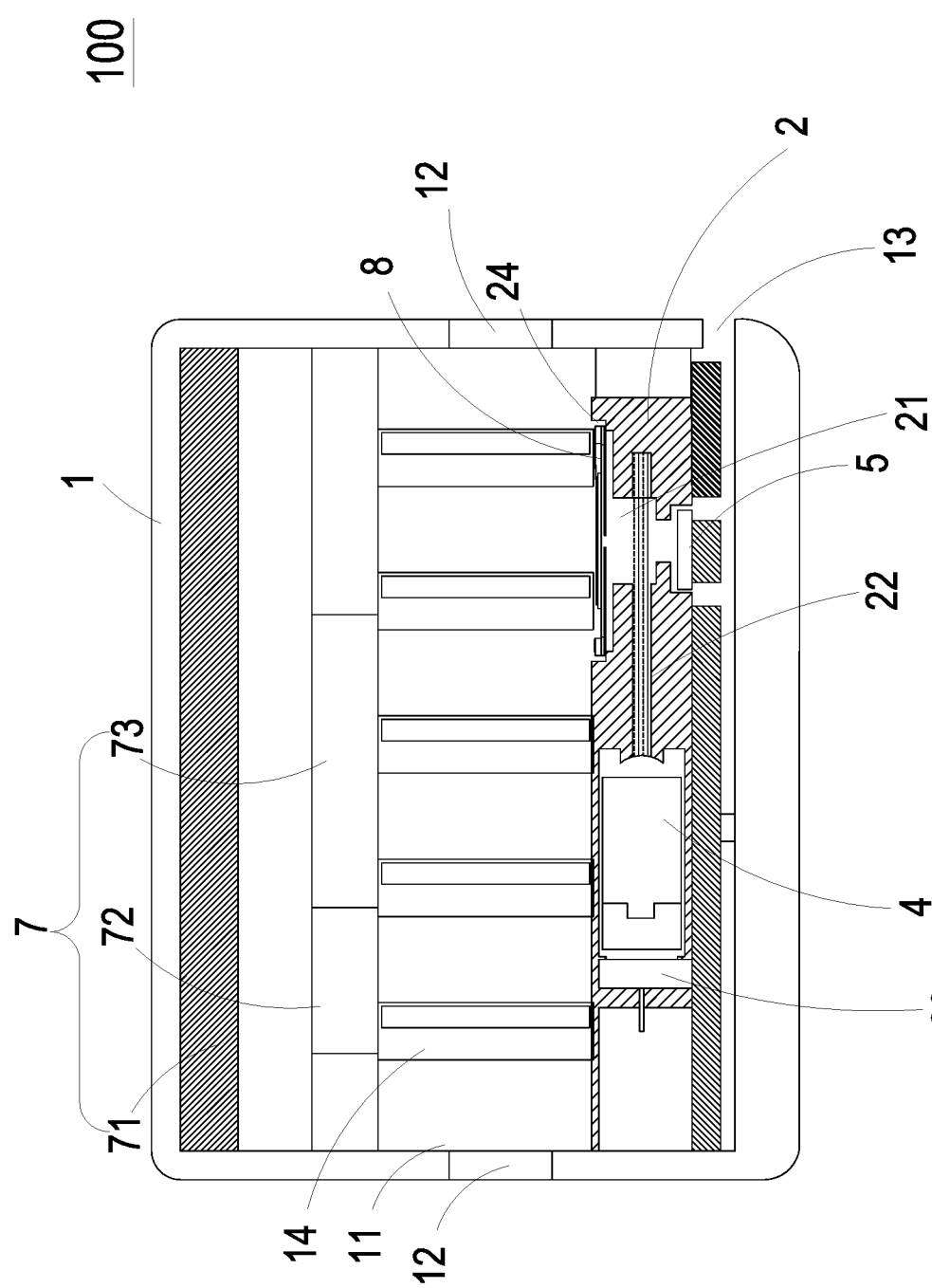
FIG. 5 is a schematic cross-sectional view illustrating a portion of a gas detecting device according to a second embodiment of the present disclosure.
Figure 6:
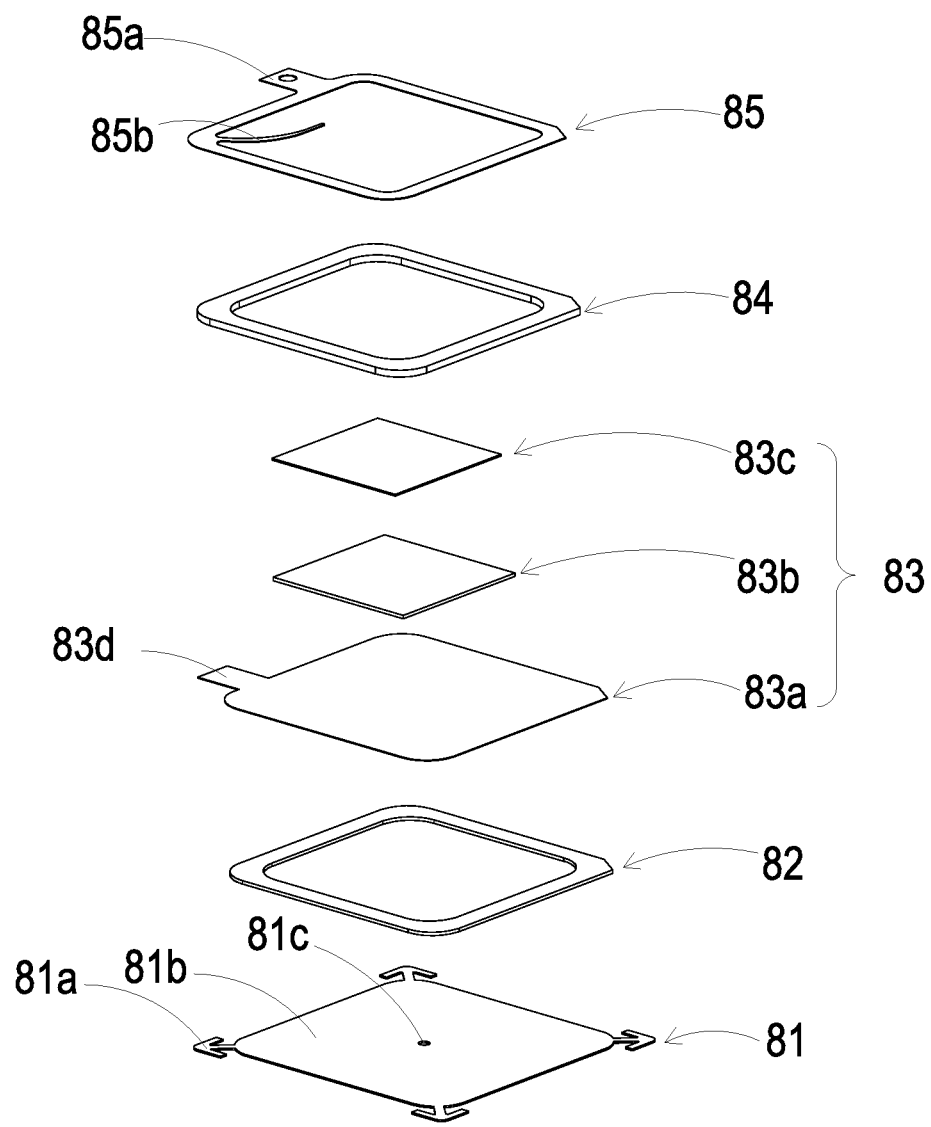
FIG. 6 is a schematic exploded view illustrating the gas transporting actuator of the gas detecting device according to the second embodiment.

Please refer to FIG. 5, which is a schematic cross-sectional view illustrating a portion of a gas detecting device according to a second embodiment of the present disclosure. In this embodiment, the gas transporting actuator 3 is a piezoelectric blower pump. In the figures, reference number 8 is assigned to the gas transporting actuator, and the piezoelectric blower pump is exemplified by the gas transporting actuator 8 in the following description. The gas transporting actuator 8 is accommodated within the accommodation slot 24 of the optical mechanism 2. Please refer to FIG. 6 and FIG. 7A. The gas transporting actuator 8 includes a nozzle plate 81, a chamber frame 82, an actuator 83, an insulating frame 84 and a conducting frame 85, which are stacked on each other sequentially. The nozzle plate 81 includes a plurality of coupling elements 81a, a suspension plate 81b and a central opening 81c. The suspension plate 81b is permitted to undergo bending vibration. The plurality of coupling elements 81a are connected to the periphery of the suspension plate 81b. In this embodiment, the nozzle plate 81 has four coupling elements 81a, and the four coupling elements 81a are connected to four corners of the suspension plate 81b, but not limited thereto. The central opening 81c runs through a middle region of the suspension plate 81b. The chamber frame 82 is carried and stacked on the suspension plate 81b. The actuator 83 is carried and stacked on the chamber frame 82 and includes a piezoelectric carrying plate 83a, an adjusting resonance plate 83b and a piezoelectric plate 83c. The piezoelectric carrying plate 83a is carried and stacked on the chamber frame 82. The adjusting resonance plate 83b is carried and stacked on the piezoelectric carrying plate 83a. The piezoelectric plate 83c is carried and stacked on the adjusting resonance plate 83b. When a voltage is applied to the piezoelectric plate 83c, the piezoelectric plate 83c deforms to drive the piezoelectric carrying plate 83a and the adjusting resonance plate 83b to bend and vibrate in a reciprocating manner. The insulating frame 84 is carried and stacked on the piezoelectric carrying plate 83a of the actuator 83. The conducting frame 85 is carried and stacked on the insulating frame 84. A resonance chamber 86 is formed among the actuator 83, the chamber frame 82 and the suspension plate 81b collaboratively. Moreover, the adjusting resonance plate 83b is thicker than the piezoelectric carrying plate 83a.

As mentioned above, the gas transporting actuator 8 is connected to a lateral side 24b of the accommodation slot 24 through four coupling elements 81a. Moreover, the gas transporting actuator 8 is spaced apart from a bottom surface 24a of the accommodation slot 24, so that an airflow chamber 87 is formed between the suspension plate 81b and the bottom surface 24a of the accommodation slot 24. Moreover, a plurality of vacant spaces 81d are formed among the suspension plate 81b, the plurality of coupling elements 81a and the lateral sides 24b of the accommodation slot 24. In addition, the piezoelectric carrying plate 83a further includes a first conductive pin 83d. The first conductive pin 83d is protruded outwardly from an outer edge of the piezoelectric carrying plate 83a. The conducting frame 85 also includes a second conductive pin 85a and an electrode 85b. The second conductive pin 85a is protruded outwardly from an outer edge of the conducting frame 85. The electrode 85b is protruded outwardly from an inner edge of the conducting frame 85. After the components of the gas transporting actuator 8 are stacked and assembled sequentially, the electrode 85b is electrically connected to the piezoelectric plate 83c, so that the first conductive pin 83d and the second conductive pin 85a receive a driving signal and a loop is formed successfully.

Figure 7A:
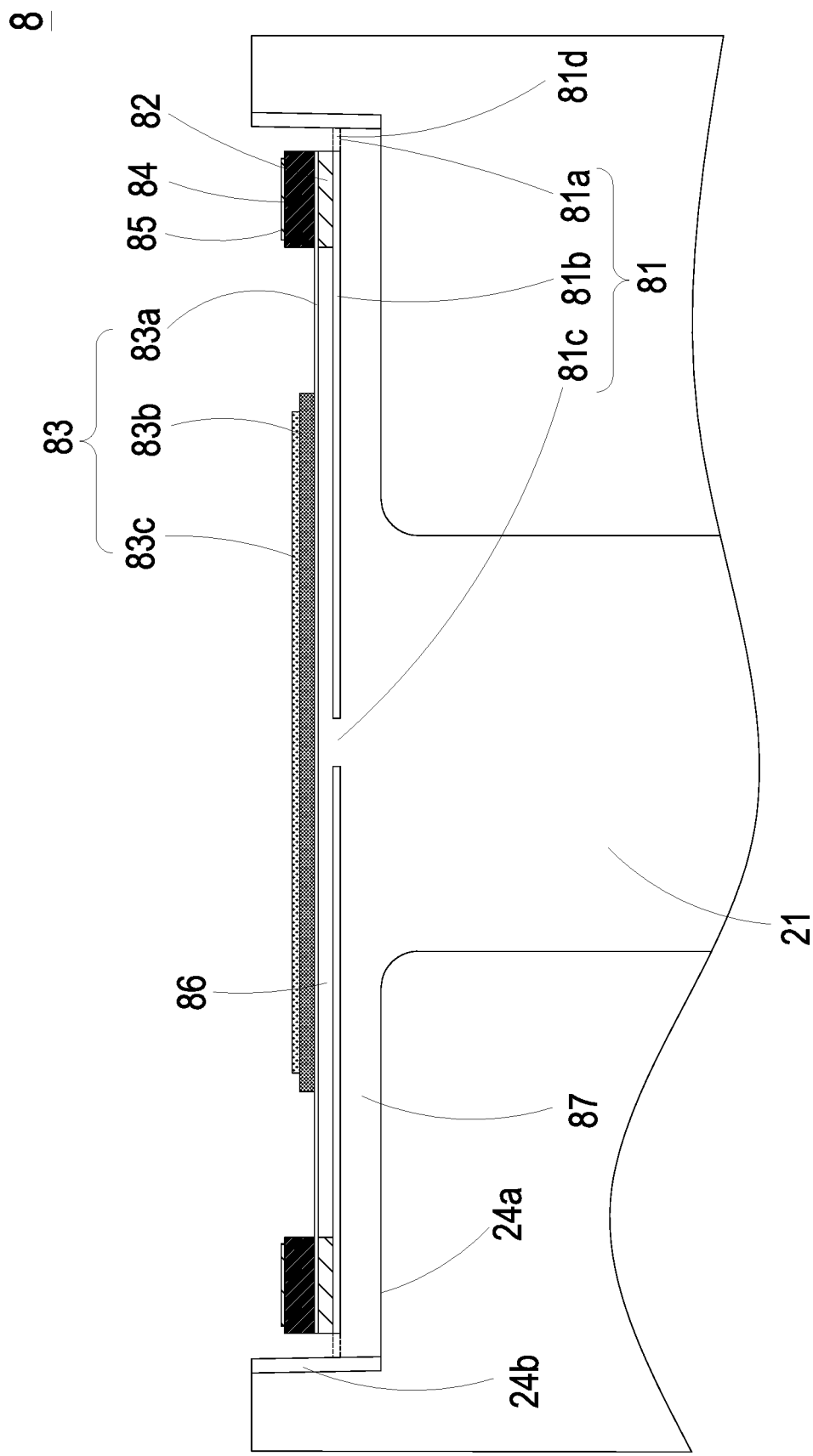
FIG. 7A is a schematic cross-sectional view illustrating a portion of the gas transporting actuator of the gas detecting device according to the second embodiment of the present disclosure.
Figure 7B:
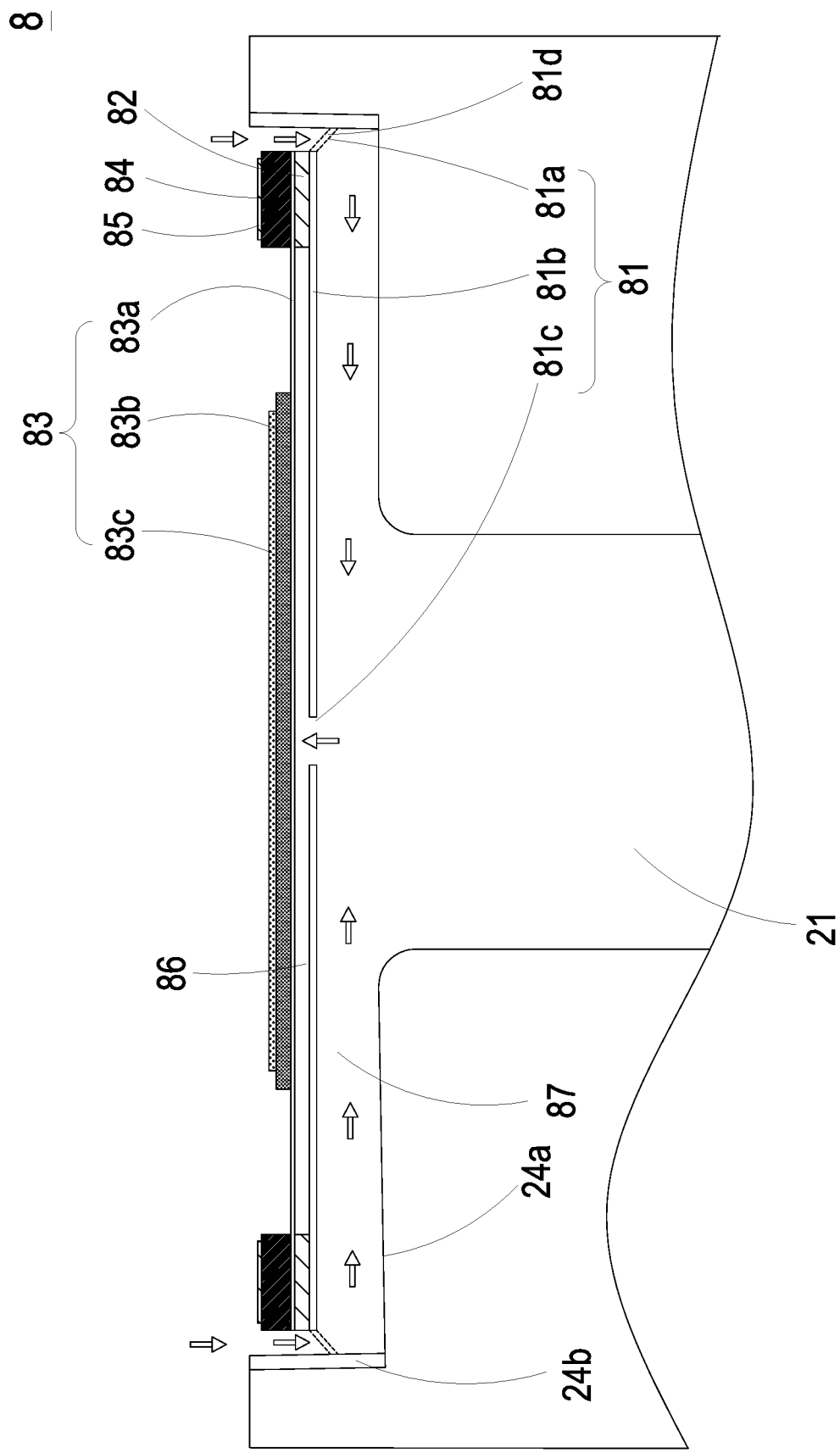
FIGS. 7B and 7C schematically illustrate the actions of the gas transporting actuator of the gas detecting device according to the second embodiment of the present disclosure.
Figure 7C:
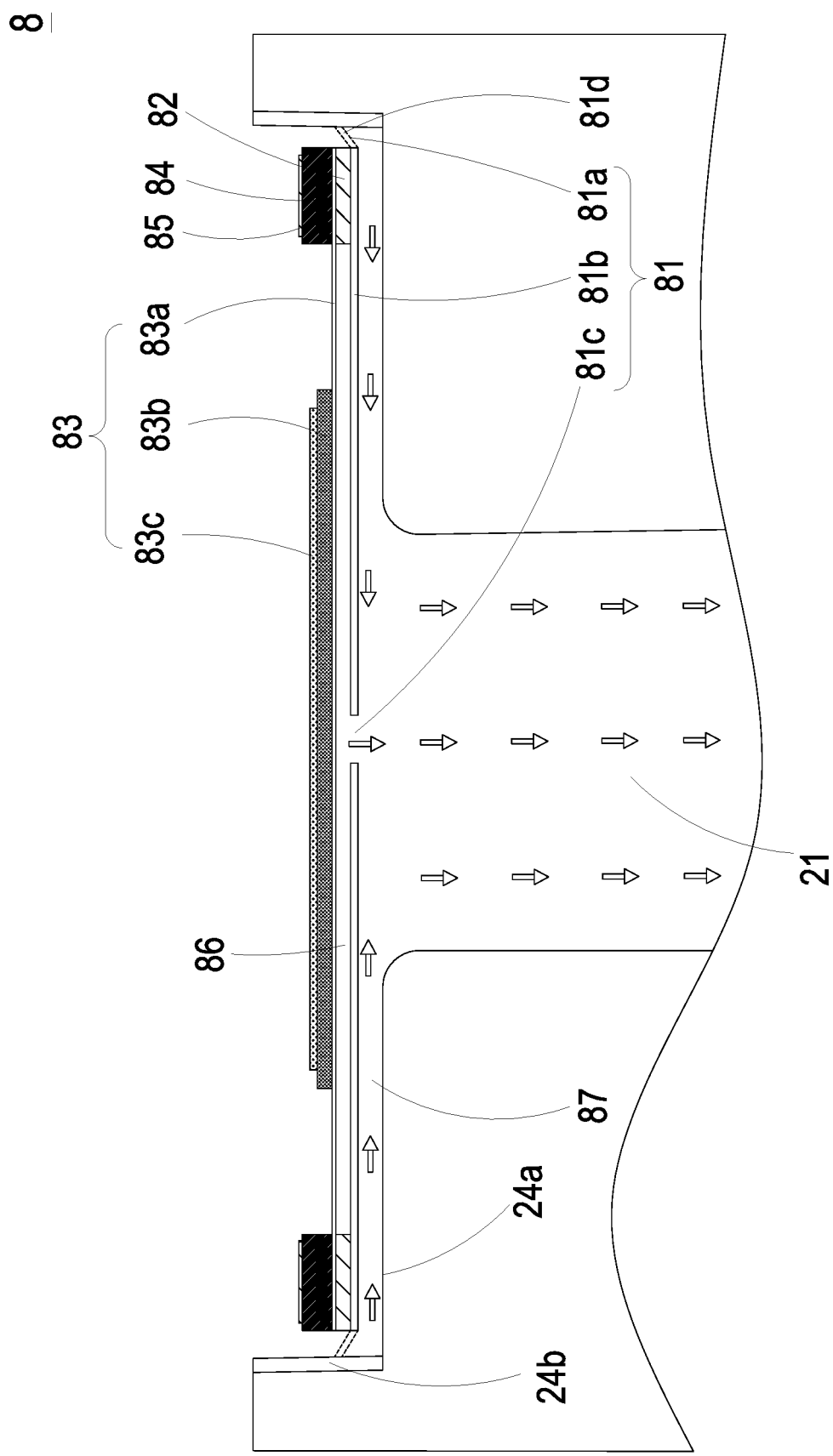

Please refer to FIGS. 7A, 7B and 7C. As shown in FIG. 7A, the gas transporting actuator 8 is disposed in the accommodation slot 24 of the optical mechanism 2. The nozzle plate 81 and the bottom surface 24a of the accommodation slot 24 are spaced apart from each other, so that the airflow chamber 87 is formed between the nozzle plate 81 and the bottom surface 24a of the accommodation slot 24. Please refer to FIG. 7B. When a voltage is applied to the piezoelectric plate 83c of the actuator 83, the piezoelectric plate 83c is subjected to deformation by the piezoelectric effect to drive the adjusting resonance plate 83b and the piezoelectric carrying plate 83a to move synchronously. Meanwhile, the nozzle plate 81 is correspondingly moved due to a Helmholtz resonance effect, and the actuator 83 is moved upwardly. Since the actuator 83 is moved upwardly, the volume of the airflow chamber 87 between the nozzle plate 81 and the bottom surface 24a of the accommodation slot 24 is expanded, and a negative pressure is formed in the airflow chamber 87. The pressure gradient allows the ambient air to be inhaled from the outside of the gas transporting actuator 8 through the vacant spaces 81d between the coupling elements 81a of the nozzle plate 81 and the lateral sides 24b of the accommodation slot 24 into the airflow chamber 87. Consequently, the pressure-collecting operation is performed. Finally, as shown in FIG. 7C, the air is continuously introduced into the airflow chamber 87 so that a positive pressure is formed the airflow chamber 87. Meanwhile, the actuator 83 is actuated to move downwardly by an applied voltage, so that the volume of the airflow chamber 87 is shrunken and the air in the airflow chamber 87 is pushed to flow toward the airflow channel 21. Then, the sizes and the concentration of the suspended particles in the air are measured by the particle detector 5. As the air in the chamber 11 is continuously inhaled by the gas transporting actuator 8, the ambient air around the casing 1 can be continuously fed into the chamber 11 and transferred to the communication channel 14. Thereby, the sensor of the external sensing module 6 senses the content of a specified gas in the air, the content of other contaminate (e.g., the bacterial content, the virus content or the microorganism content) or the environment condition (e.g., temperature or humidity).

Figure 8:
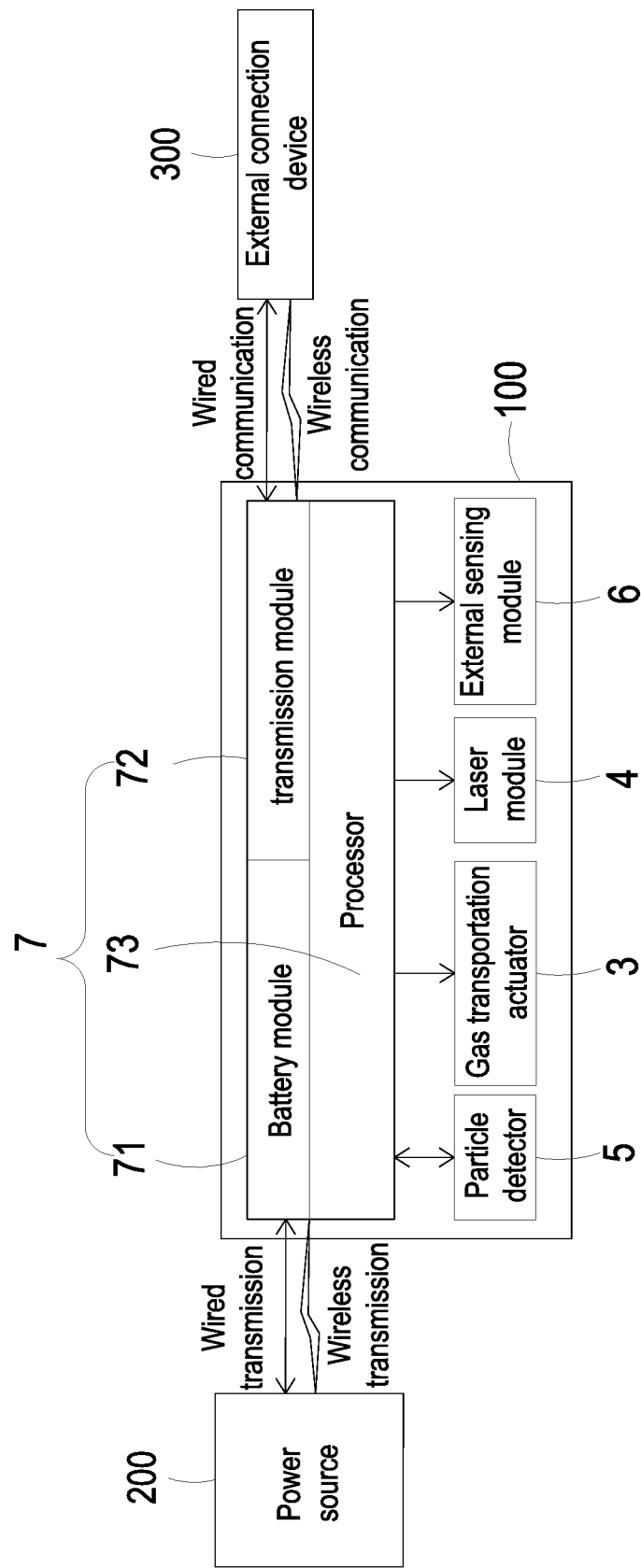
FIG. 8 is a functional block diagram illustrating the architecture of a gas detecting system according to an embodiment of the present disclosure.

Please refer to FIGS. 1 and 8. The gas detecting device 100 further includes a driving module 7. The driving module 7 includes a battery module 71 for storing electric power and providing the electric power to the gas transporting actuator 3, the laser module 4, the particle detector 5 and the external sensing module 6. The battery module 71 is electrically connected to an external power source 200 for receiving the electric power from the power source 200 and storing the electric power. The external power source 200 can transfer the electric power to the battery module 71 in a wired transmission manner or a wireless transmission manner, but not limited thereto.

Please refer to FIGS. 1 and 8 again. The driving module 7 further includes a communication module 72 and a processor 73. The processor 73 is electrically connected to the battery module 71, the communication module 72, the gas transporting actuator 3, the laser module 4 and the particle detector 5 and is used to actuate the gas transporting actuator 3, the laser module 4 and the particle detector 5. The external sensing module 6 is detachably installed in the communication channel 14, and is electrically connected to and in signal communication with the processor 73. Therefore, the detection results of the particle detector 5 and the sensor of the external sensing module 6 are analyzed, calculated, stored and converted by the processor 73 to obtain a monitored value. When the gas transporting actuator 3 is actuated by the processor 73, the gas transporting actuator 3 inhales the ambient air into the airflow channel 21. The light beam emitted from the laser module 4 to the light-beam channel 22 is projected on the air within the airflow channel 21. In such way, the particle detector 5 detects a plurality of light spots, which are generated by the suspended particles in the airflow channel 73 irradiated by the light beam, and transmits the detection result to the processor 73. According to the detection result, the processor 73 calculates the sizes and the concentration of the suspended particles in the air and analyzes to generate a monitored value for storing. The monitored value stored in the processor 73 is transmitted to an external connection device 300 through the communication module 72. The external connection device 300 is at least one selected from the group consisting of a cloud system, a portable electronic device, a computer system, a display device and combination thereof. The monitored value and the warning message are displayed through the external connection device 300.

When the gas transporting actuator 3 is actuated by the processor 73, the air in the chamber 11 is transferred to the airflow channel 21 by the gas transporting actuator 3, so that a negative pressure is formed in the chamber 11 and the ambient air around the casing 1 is inhaled through the inlet 12 into the chamber 11. Meanwhile, the air in the chamber 11 is transferred to the communication channel 14. The air in the communication channel 14 is detected by the sensor of the external sensing module 6 in the communication channel 14, and the detection result is transmitted to the processor 73. According to the detection result, the processor 73 calculates the content of a specified gas in the air, the content of other contaminate (e.g., the bacterial content, the virus content or the microorganism content) or the environment condition (e.g., temperature or humidity) and analyzes to generate a monitored value for storing. The monitored value stored in the processor 73 is transmitted to an external connection device 300 through the communication module 72.

The communication module 72 is in signal communication with the external connection device 300 in a wired communication manner or a wireless communication manner. The wired communication manner can be at least one selected from the group consisting of a USB communication module, a mini-USB communication module, a micro-USB communication module and combinations thereof. The wireless communication manner can be at least one selected from the group consisting of a Wi-Fi communication module, a Bluetooth communication module, a radio frequency identification (RFID) communication module, a near field communication (NFC) communication module and combinations thereof.

From the above descriptions, the present disclosure provides the gas detecting device. The gas detecting device includes the gas transporting actuator for guiding the air in the chamber to the airflow channel. When the light beam from the laser module is projected on the air within the airflow channel, the suspended particles in the air are irradiated by the light beam to generate a plurality of light spots and the particle detector detects those light spots. According to the detection result, the sizes and the concentration of the suspended particles in the air are measured. In addition, as the air in the chamber is continuously transferred by the gas transporting actuator to the airflow channel, a negative pressure is formed in the chamber continuously, so that the ambient air can be continuously inhaled through the inlet into the chamber and transferred to the communication channel in fluid communication with the chamber. Thereby, the sensor of the external sensing module in the communication channel senses the content of a specified gas in the air, the content of other contaminate (e.g., the bacterial content, the virus content or the microorganism content) or the environment condition (e.g., temperature or humidity). Since the external sensing module is detachably installed in the communication channel, the sensor may be replaced and selected according to the practical requirements. In case that the sensor is damaged, the sensor can be replaced with a new one. That is, it is not necessary to send the whole gas detecting device to the original factory for repair or purchase the new gas detecting device.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device, comprising:
   a casing comprising a chamber, at least one inlet, an outlet and at least one communication channel, wherein the chamber is in fluid communication with the inlet, the outlet and the communication channel;

an optical mechanism disposed in the chamber, and comprising an airflow channel and a light-beam channel, wherein the airflow channel is in fluid communication with the inlet and the outlet, and the light-beam channel is in communication with the airflow channel;

a gas transporting actuator comprising a gas inlet plate, a resonance plate and a piezoelectric actuator, wherein the gas transporting actuator is disposed on the optical mechanism, wherein when the gas transporting actuator is actuated, ambient air is introduced through the inlet into the chamber and transferred through the communication channel to the airflow channel;

a laser module disposed in the optical mechanism and configured to emit a light beam through the light-beam channel to the airflow channel;

a particle detector disposed in the airflow channel and located at a first end of the airflow channel away from the gas transporting actuator, the particle detector detecting a plurality of light spots caused by the suspended particles in the air after the light beam from the laser module being projected on the air within the airflow channel and accordingly calculating sizes and a concentration of the suspended particles in the air; and at least one external sensing module detachably installed in the communication channel, and comprising a sensor for measuring the air in the communication channel, wherein the gas inlet plate, the resonance plate and the piezoelectric actuator are stacked sequentially, and a chamber space is formed between the resonance plate and the piezoelectric actuator so that the air is inhaled through the gas inlet plate when the piezoelectric actuator is enabled, whereby the air is further transferred through the resonance plate.

2. The gas detecting device according to claim 1, wherein the optical mechanism further comprises a light-source receiving slot and an accommodation slot, wherein the light-source receiving slot is in communication with the light-beam channel, and the accommodation slot is disposed in the airflow channel and located at a second end of the airflow channel away from the particle detector, wherein the gas transporting actuator is accommodated within the accommodation slot of the optical mechanism and configured to transport the air to the airflow channel, and the laser module is accommodated within the light-source receiving slot of the optical mechanism to emit the light beam to the light-beam channel.

3. The gas detecting device according to claim 1, wherein the suspended particle detected by the particle sensor is at least one selected from the group consisting of a PM2.5 suspended particle, a PM10 suspended particle and combinations thereof.

4. The gas detecting device according to claim 1, wherein while a cleaning process is performed, the gas transporting actuator is actuated to eject the air to the airflow channel at a high speed, so that the suspended particles on an exterior surface of the particle detector are blown away, thereby maintaining the detecting accuracy of the particle detector.

5. The gas detecting device according to claim 1, further comprising:

a processor configured to actuate the gas transporting actuator, the laser module, the particle detector and the external sensing module, wherein after a detection result of the particle detector and a detection result of the sensor of the external sensing module are analyzed by the processor, a monitored value is obtained; and a communication module configured to transmit the monitored value to an external connection device, so that the monitored value and a warning message are displayed through the external connection device.

6. The gas detecting device according to claim 5, wherein the communication module is a wired communication module or a wireless communication module.

7. The gas detecting device according to claim 5, wherein the external connection device is at least one selected from the group consisting of a cloud system, a portable electronic device, a computer system and combinations thereof.

8. The gas detecting device according to claim 5, further comprising a battery module configured to store electric power and provide the electric power to the gas transporting actuator, the laser module, the particle detector and the sensor of the external sensing module, wherein the battery module receives the electric power from a power source for storing.

9. The gas detecting device according to claim 1, wherein:

the gas inlet plate has at least one inlet aperture, at least one convergence channel and a convergence chamber, wherein the at least one inlet aperture allows air to flow in, and wherein the convergence channel is disposed corresponding to the at least one inlet aperture and guides the air from the at least one inlet aperture toward the convergence chamber;

the resonance plate has a central aperture and a movable part, wherein the central aperture is aligned with the convergence chamber, and the movable part surrounds the central aperture; and the piezoelectric actuator is aligned with the resonance plate, wherein the air is inhaled through the at least one inlet aperture of the gas inlet plate to the at least one convergence channel, is converged to the convergence chamber and flows into the chamber space through the central aperture of the resonance plate when the piezoelectric actuator is enabled, whereby the air is further transferred through a resonance effect between the piezoelectric actuator and the movable part of the resonance plate.

10. The gas detecting device according to claim 9, wherein the piezoelectric actuator comprises:

a suspension plate having a square profile, wherein the suspension plate is permitted to undergo a bending vibration;

an outer frame arranged around the suspension plate;

at least one bracket connected between the suspension plate and the outer frame for elastically supporting the suspension plate; and a piezoelectric element, wherein a length of a side of the piezoelectric element is smaller than or equal to a length of a side of the suspension plate, and the piezoelectric element is attached on a surface of the suspension plate, wherein when a voltage is applied to the piezoelectric element, the suspension plate is driven to undergo the bending vibration.

11. The gas detecting device according to claim 9, wherein the gas transporting actuator further comprises a first insulation plate, a conducting plate and a second insulation plate, wherein the gas inlet plate, the resonance plate, the piezoelectric actuator, the first insulation plate, the conducting plate and the second insulation plate are stacked sequentially.

12. The gas detecting device according to claim 1, wherein the sensor of the external sensing module is at least one selected from the group consisting of an oxygen sensor, a carbon monoxide sensor, a carbon dioxide sensor, a bacterial sensor, a virus sensor, a microorganism sensor, a temperature sensor, a humidity sensor and combinations thereof.

13. The gas detecting device according to claim 1, wherein the sensor of the external sensing module is a volatile organic compound sensor.

14. The gas detecting device according to claim 5, wherein the sensor of the external sensing module in installed in the communication channel, and the sensor is electrically connected to and in signal communication with the processor.

15. A gas detecting device, comprising:
   at least one casing comprising at least one chamber, at least one inlet, at least one outlet and at least one communication channel, wherein the chamber is in fluid communication with the inlet, the outlet and the communication channel;
   at least one optical mechanism disposed in the chamber, and comprising at least one airflow channel and at least one light-beam channel, wherein the airflow channel is in fluid communication with the inlet and the outlet, and the light-beam channel is in communication with the airflow channel;
   at least one gas transporting actuator comprising a nozzle plate, a chamber frame, an actuator, an insulating frame and a conducting frame, wherein the nozzle plate comprises a suspension plate and the gas transporting actuator is disposed on the optical mechanism, wherein when the gas transporting actuator is actuated, ambient air is introduced through the inlet into the chamber and transferred through the communication channel to the airflow channel;
   at least one laser module disposed in the optical mechanism and configured to emit a light beam through the light-beam channel to the airflow channel;
   at least one particle detector disposed in the airflow channel and located at a first end of the airflow channel away from the gas transporting actuator, the particle detector detecting a plurality of light spots caused by the suspended particles in the air after the light beam from the laser module being projected on the air within the airflow channel and accordingly calculating sizes and a concentration of the suspended particles in the air; and
   at least one external sensing module detachably installed in the communication channel, and comprising at least one sensor for measuring the air in the communication channel,
   wherein a resonance chamber is defined by the actuator, the chamber frame and the suspension plate collaboratively, wherein by driving the actuator to drive the nozzle plate to generate a resonance, the suspension plate of the nozzle plate vibrates in the reciprocating manner, thereby air transportation is achieved.

16. A gas detecting device, comprising:
   a casing comprising a chamber, at least one inlet, an outlet and at least one communication channel, wherein the chamber is in fluid communication with the inlet, the outlet and the communication channel;
   an optical mechanism disposed in the chamber, and comprising an airflow channel and a light-beam channel, wherein the airflow channel is in fluid communication with the inlet and the outlet, and the light-beam channel is in communication with the airflow channel;
   a gas transporting actuator comprising a nozzle plate, a chamber frame, an actuator, an insulating frame and a conducting frame, wherein the nozzle plate comprises a suspension plate and the gas transporting actuator is disposed on the optical mechanism, wherein when the gas transporting actuator is actuated, ambient air is introduced through the inlet into the chamber and transferred through the communication channel to the airflow channel;
   a laser module disposed in the optical mechanism and configured to emit a light beam through the light-beam channel to the airflow channel;
   a particle detector disposed in the airflow channel and located at a first end of the airflow channel away from the gas transporting actuator, the particle detector detecting a plurality of light spots caused by the suspended particles in the air after the light beam from the laser module being projected on the air within the airflow channel and accordingly calculating sizes and a concentration of the suspended particles in the air; and
   at least one external sensing module detachably installed in the communication channel, and comprising a sensor for measuring the air in the communication channel,
   wherein a resonance chamber is defined by the actuator, the chamber frame and the suspension plate collaboratively, wherein by driving the actuator to drive the nozzle plate to generate a resonance, the suspension plate of the nozzle plate vibrates in the reciprocating manner, thereby air transportation is achieved.

17. The gas detecting device according to claim 16, wherein the optical mechanism further comprises a light-source receiving slot and an accommodation slot, wherein the light-source receiving slot is in communication with the light-beam channel, and the accommodation slot is disposed in the airflow channel and located at a second end of the airflow channel away from the particle detector, wherein the gas transporting actuator is accommodated within the accommodation slot of the optical mechanism and configured to transport the air to the airflow channel, and the laser module is accommodated within the light-source receiving slot of the optical mechanism to emit the light beam to the light-beam channel.

18. The gas detecting device according to claim 17, wherein:
   the nozzle plate comprises a plurality of coupling elements, the suspension plate and a central opening, wherein the suspension plate is permitted to undergo bending vibration, and the plurality of coupling elements are connected to the accommodation slot, so that the nozzle plate is positioned and accommodated within the accommodation slot and an airflow chamber is formed between the nozzle plate and a bottom surface of the accommodation slot, wherein at least one vacant space is formed among the plurality of coupling elements, the suspension plate and the accommodation slot;
   the chamber frame is carried and stacked on the suspension plate;
   the actuator is carried and stacked on the chamber frame, wherein when a voltage is applied to the actuator, the actuator undergoes a bending vibration in a reciprocating manner;
   the insulating frame is carried and stacked on the actuator; and
   the conducting frame is carried and stacked on the insulating frame, wherein the air is transferred through the at least one vacant space to the airflow chamber and then discharged from the outlet, thereby achieving air transportation.

19. The gas detecting device according to claim 16, wherein the actuator comprises:
   a piezoelectric carrying plate carried and stacked on the chamber frame;
   an adjusting resonance plate carried and stacked on the piezoelectric carrying plate; and
   a piezoelectric plate carried and stacked on the adjusting resonance plate, wherein when the voltage is applied to the piezoelectric plate, the piezoelectric plate drives the piezoelectric carrying plate and the adjusting resonance plate to bend and vibrate in the reciprocating manner.

20. The gas detecting device according to claim 19, wherein the adjusting resonance plate is thicker than the piezoelectric carrying plate.

* * * * *